United States Patent [19]

Takeno et al.

[11] 4,105,436
[45] Aug. 8, 1978

[54] HERBICIDE

[75] Inventors: Tsuneyuki Takeno; Tetsuji Iwasaki, both of Wakayama; Norioki Miyamoto; Kyozaburo Tachibana, both of Sakura; Masamoto Matsukane, Funabashi, all of Japan

[73] Assignee: Kao Soap Co., Ltd., Tokyo, Japan

[21] Appl. No.: 822,548

[22] Filed: Aug. 8, 1977

[30] Foreign Application Priority Data

Oct. 18, 1976 [JP] Japan .................. 51/124602

[51] Int. Cl.² .............................................. A01N 9/14
[52] U.S. Cl. .................................................... 71/103
[58] Field of Search ........................................ 71/103

[56] References Cited

U.S. PATENT DOCUMENTS

| 3,159,666 | 12/1964 | Heininger et al. | 71/103 |
| 3,799,760 | 3/1974 | Stephens | 71/103 |
| 3,907,853 | 9/1975 | Fridinger | 71/103 X |
| 3,941,826 | 3/1976 | Martin | 71/103 X |

OTHER PUBLICATIONS

Maccagnani et al., Chem. Abst., vol. 69, (1968) 86143h.

Primary Examiner—Catherine L Mills
Attorney, Agent, or Firm—Oblon, Fisher, Spivak, McClelland &Maier

[57] ABSTRACT

A herbicide which comprises at least one compound as an active ingredient of the formula (I);

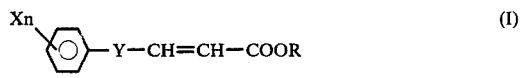

wherein X represents a halogen atom or an alkyl sulfinyl or alkyl sulfonyl group having 1 to 3 carbon atoms, $n$ represents an integer of 0 – 3, Y represents SO or SO$_2$, and R represents a hydrogen atom or an alkyl group having 1 to 3 carbon atoms.

9 Claims, No Drawings

HERBICIDE

BACKGROUND OF THE INVENTION

The present invention relates to a novel herbicide. More particularly, the invention relates to a herbicide which comprises at least one compound as an active ingredient of the formula (I);

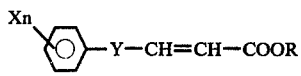  (I)

wherein X represents a halogen atom or an alkyl sulfinyl or alkyl sulfonyl having 1 to 3 carbon atoms, $n$ represents an integer of 1 to 3, Y represents SO or SO2, and R represents a hydrogen atom or an alkyl group having 1 to 3 carbon atoms.

A wide variety of compounds have been examined. As a result of the investigation, it has been found that the compounds of formula (I) according to this invention exhibit excellent herbicidal effects on a large number of weeds as well as high stability for crops. Moreover, the present compounds are very safe and are of substantially reduced toxicity to human beings, animals, fish, shell-fish and the like.

SUMMARY OF THE INVENTION

Accordingly, one object of the present invention is to provide a novel herbicide which has excellent herbicidal effects and high safety.

DETAILED DESCRIPTION OF THE PREFERRED EMBODIMENTS

The following compounds are specific active ingredients within the scope of the present invention. Parenthesized are the melting points of the exemplified compounds.

1) Cl—⟨◯⟩—SO—CH=CH—COOCH₃  (55–56° C)

2) 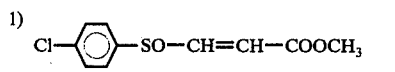  (58–59° C)

3) 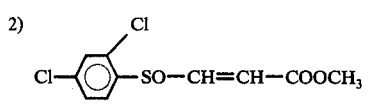  (63–64° C)

4) 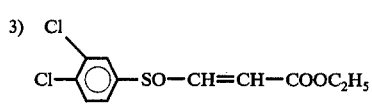  (49–50° C)

5)   (57–58° C)

6) CH₃SO—⟨◯⟩—SO—CH=CH—COOH  (72–73° C)

7) 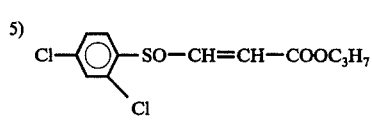  (78–79° C)

8) Cl—⟨◯⟩—SO₂—CH=CH—COOCH₃  (90–91° C)

9) Cl—⟨◯⟩—SO₂—CH=CH—COOC₃H₇  (92–93° C)

10) 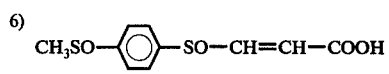  (88–89° C)

11)   (93–94° C)

12) 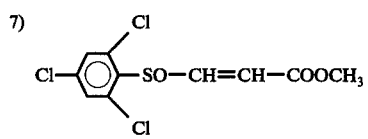  (101–102° C)

13) CH₃SO₂—⟨◯⟩—SO₂—CH=CH—COOH  (90–91° C)

The present compounds of formula (I) can be prepared by any conventional techniques, one of which is described hereinafter.

A mercaptan of the formula (II);

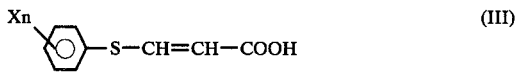  (II)

wherein Xn is the same as in formula (I), is reacted with an acetylene monocarboxylic acid in an alkaline aqueous solution whereby a compound is obtained which is represented by the formula (III);

  (III)

wherein Xn is the same as above. Thereafter, the compound of formula (III) or an acid halide thereof is allowed to react with an alcohol of the formula (IV);

ROH  (IV)

wherein R is the same as in formula (I), in the presence of an acidic or basic catalyst, thereby yielding an ester of the formula (V);

  (V)

wherein Xn and R are the same as above, and the ester of formula (V) is oxidized by an inorganic or organic peroxide such as sodium metaperiodate, hydrogen peroxide, perbenzoic acid, m-chloroperbenzoic acid and peracetic acid, whereby a compound of formula (I) is obtained.

The compounds of formula (I) of the present invention exhibit excellent herbicidal effects particularly when applied to the stems and leaves of gramineae weeds such as barnyardgrass, *Cyperus microiria*, henry crabgrass, goosegrass and green foxtail; broad-leaved weeds such as *Chenopodium album var. centrorubrum*,

*Polygonum blumei*, livid amaranth, common purslane, common lambsquarters and *Commelina communis;* and perennial weeds such as *Rumex japonicus* and pink woodsorrel, all of which grow in fields and paddy fields. The present compounds are noted to be very safe and harmless to the crops.

The compounds of formula (I) can be applied in the forms of hydrates, emulsions, powders, granules and the like by dissolving, suspending, emulsifying the compounds in carriers or by mixing the compounds with an adjuvant. The present compounds may be normally employed in a concentration ranging from 3,000 to 6,000 ppm, preferably 4,000 ppm. Suitable solid carriers which are useful as adjuvants include mineral powders of clays such as bentonite, kaolin; talcs such as talcum powder; and silicates such as diatomaceous earth. Suitable liquid carriers which are useful as adjuvants include benzene, acetone, xylene, cyclohexanone and alcohols.

The herbicide of this invention may be used, if necessary, in combination with other herbicides, germicides and the like.

Having generally described this invention, a further understanding can be obtained by reference to certain preferred examples which are provided herein for purposes of illustration only and are not intended to be limiting unless otherwise specified.

EXAMPLE 1

Twenty five parts by weight of

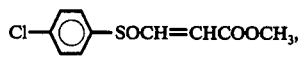

5 parts by weight of a diisobutylene-disodium maleate copolymer powder and 70 parts by weight of clay are sufficiently pulverized and mixed, thereby yielding a hydrate.

EXAMPLE 2

Forty parts by weight of

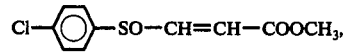

20 parts by weight of polyoxyethylene (20) sorbitan monooleate and 40 parts by weight of cyclohexane are sufficiently mixed whereby an emulsion is obtained.

EXAMPLE 3

In a series of plastic pots each having 15cm in length, 10cm in width and 8cm in depth was placed field soil. Each of the pots was planted with 20 grains of seeds of each crop listed in Table 1. On the 12th day after the seeds were covered with the soil in the pots, a test compound solution was sprayed on the whole surface of the plants in a quantity of 15ml per pot which corresponded to 500g of the active ingredient per 10 are. On the 14th day after spraying, the inhibitory effect and the possible harmful effect of the active compound were investigated on the weeds and crops. The results are shown in Table 1. It is readily understood from the results that the compounds of formula (I) of the present invention exhibit highly excellent herbicidal effects as compared to the existing herbicides.

Table 1

| Test Compounds | Inhibitory Effect on Weeds | | | | | | | Phytotoxicity to crops | | | |
|---|---|---|---|---|---|---|---|---|---|---|---|
| | Henry crab-grass | Green fox-tail | Livid ama-ranth | Poly-gonum blumei | Common lanbs-quar-ters | Common purs-lane | Rumex ja-poni-cus | Corn | Red bean | Soy-bean | Pea-nut |
| Cl—⟨○⟩—SO—CH=CH—COOCH$_3$ | 5 | 5 | 5 | 5 | 5 | 5 | 5 | 0 | 0 | 0 | 0 |
| Cl—⟨○⟩—SO—CH=CH—COOC$_3$H$_7$ | 5 | 5 | 5 | 5 | 5 | 5 | 5 | 0 | 0 | 0 | 0 |
| Br—⟨○⟩—SO—CH=CH—COOCH$_3$ | 5 | 5 | 5 | 5 | 5 | 5 | 5 | 0 | 0 | 0 | 0 |
| CH$_3$SO—⟨○⟩—SO—CH=CH—COOCH$_3$ | 5 | 5 | 5 | 5 | 5 | 5 | 5 | 0 | 0 | 0 | 0 |
| Cl,Cl—⟨○⟩—SO—CH=CH—COOC$_2$H$_5$ | 5 | 5 | 4 | 4.5 | 4.5 | 4 | 4 | 0 | 0 | 1 | 0 |
| Present Compounds: Cl—⟨○⟩(Cl)—SO—CH=CH—COOH | 5 | 5 | 4.5 | 4.5 | 4.5 | 4.5 | 4.5 | 0 | 1 | 1 | 0 |
| Cl—⟨○⟩(Cl)—SO—CH=CH—COOC$_3$H$_7$ | 4.5 | 4.5 | 4 | 4 | 4 | 4 | 4 | 0 | 0 | 0 | 0 |

Table 1-continued

| Test Compounds | Inhibitory Effect on Weeds | | | | | | | Phytotoxicity to crops | | | |
|---|---|---|---|---|---|---|---|---|---|---|---|
| | Henry crabgrass | Green foxtail | Livid amaranth | Polygonum blumei | Common lanbsquarters | Common purslane | Rumex japonicus | Corn | Red bean | Soybean | Peanut |
| 2,6-Br₂-C₆H₃-SO-CH=CH-COOCH₃ | 5 | 5 | 4.5 | 4.5 | 4.5 | 4.5 | 4.5 | 0 | 1 | 1 | 0 |
| 2,4,6-Cl₃-C₆H₂-SO-CH=CH-COOCH₃ | 4 | 4 | 4 | 4 | 4 | 4 | 3 | 0 | 0 | 0 | 0 |
| 2,4,6-Cl₃-C₆H₂-SO-CH=CH-COOC₂H₅ | 4 | 4 | 4 | 4 | 4 | 4 | 3 | 0 | 0 | 0 | 0 |
| 4-Cl-C₆H₄-SO₂-CH=CH-COOCH₃ | 4 | 4 | 2 | 2 | 2 | 2 | 2 | 0 | 0 | 0 | 0 |
| 4-Cl-C₆H₄-SO₂-CH=CH-COOC₂H₅ | 4 | 4 | 2 | 2 | 2 | 2 | 1 | 0 | 0 | 0 | 0 |
| 3,4-Cl₂-C₆H₃-SO₂-CH=CH-COOCH₃ | 3 | 3 | 2 | 2 | 2 | 2 | 2 | 0 | 0 | 0 | 0 |
| 2,4-Cl₂-C₆H₃-SO₂-CH=CH-COOCH₃ | 3 | 3 | 2 | 2 | 2 | 2 | 2 | 0 | 0 | 0 | 0 |
| 2,4-Cl₂-C₆H₃-SO₂-CH=CH-COOC₃H₇ | 2 | 2 | 1 | 1 | 1 | 1 | 0 | 0 | 0 | 0 | 0 |
| 2,4,6-Cl₃-C₆H₂-SO₂-CH=CH-COOH | 2 | 2 | 0 | 0 | 0 | 0 | 0 | 0 | 0 | 0 | 0 |
| 4-CH₃SO₂-C₆H₄-SO₂-CH=CH-COOH | 2 | 2 | 1 | 0 | 0 | 0 | 0 | 0 | 0 | 0 | 0 |
| Control Compounds: 4-Cl-C₆H₄-S-CH=CH-COOC₂H₅ | 0 | 0 | 0 | 0 | 0 | 0 | 0 | 0 | 0 | 0 | 0 |
| C₆H₅-CH₂S-CH=CH-COOH | 0 | 0 | 0 | 0 | 0 | 0 | 0 | 0 | 0 | 0 | 0 |
| 4-CH₃-C₆H₄-S-CH=CH-COOC₂H₅ | 0 | 0 | 0 | 0 | 0 | 0 | 0 | 0 | 0 | 0 | 0 |

Table 1-continued

| Test Compounds | Inhibitory Effect on Weeds | | | | | | | Phytotoxicity to crops | | | |
|---|---|---|---|---|---|---|---|---|---|---|---|
| | Henry crabgrass | Green foxtail | Livid amaranth | Polygonum blumei | Common lanbsquarters | Common purslane | Rumex japonicus | Corn | Red bean | Soybean | Peanut |
| n-C₄H₉OCH=CH—COOC₄H₉ | 0 | 0 | 0 | 0 | 0 | 0 | 0 | 0 | 0 | 0 | 0 |

The definitions of the numerical rating systems in Table 1 are as follows:
Inhibitory effects on weeds
5 : perfect inhibition
4 : 80% inhibition
3 : 60% inhibition
2 : 40% inhibition
1 : 20% inhibition
0 : no effect
Phytotoxicity to crops
4 : withering
3 : severe harm
2 : moderate harm
1 : slight harm
0 : no effect

What is claimed as new and intended to be secured by Letters Patent is:

1. A method of controlling weeds which comprises applying thereto an effective amount of at least one compound of the formula;

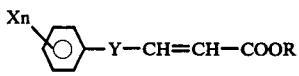

wherein X represents a halogen atom or an alkyl sulfinyl or alkyl sulfonyl group having 1 to 3 carbon atoms, n represents an integer of 0 to 3, Y represents SO or SO₂, and R represents a hydrogen atom or an alkyl group having 1 to 3 carbon atoms.

2. The method of claim 1, wherein said compound has the formula;

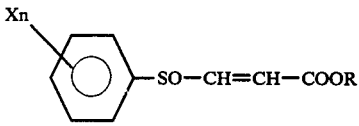

wherein X represents a halogen atom or an alkyl sulfinyl or alkyl sulfonyl group having 1 to 3 carbon atoms, n represents an integer of 0 to 3, and R represents a hydrogen atom or an alkyl group having 1 to 3 carbon atoms.

3. The method of claim 2, wherein R is a methyl group.

4. The method of claim 2, wherein the active ingredient is a compound of the formula;

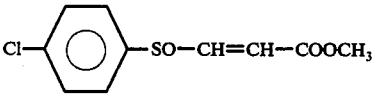

5. The method of claim 2, wherein said compound has the formula;

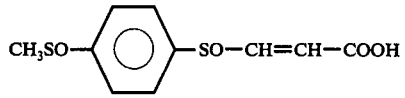

6. The method of claim 1, wherein said compound has the formula;

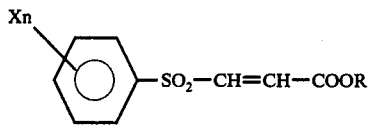

wherein X represents a halogen atom or an alkyl sulfinyl or alkyl sulfonyl group having 1 to 3 carbon atoms, n represents an integer of 0 to 3, and R represents a hydrogen atom or an alkyl group having 1 to 3 carbon atoms.

7. The method of claim 6, wherein R is a methyl group.

8. The method of claim 6, wherein the active ingredient is a compound of the formula;

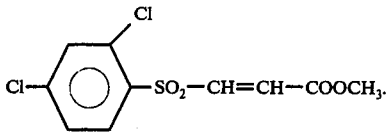

9. The method of claim 6, wherein the active ingredient is a compound of the formula;

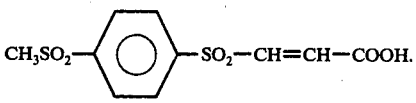

* * * * *